United States Patent

Johnson, III et al.

[11] Patent Number: 6,093,230
[45] Date of Patent: Jul. 25, 2000

[54] FILTER ASSEMBLY COMPRISING TWO FILTER ELEMENTS SEPARATED BY A HYDROPHOBIC FOAM

[75] Inventors: Harold R. Johnson, III, Flint; Robert A. Horick, Jr., Tyler, both of Tex.

[73] Assignee: Allegiance Corporation, McGaw Park, Ill.

[21] Appl. No.: 09/169,885

[22] Filed: Oct. 12, 1998

[51] Int. Cl.$^7$ ............................ B01D 46/10; A61M 1/00
[52] U.S. Cl. ........................ 55/482; 55/483; 604/319
[58] Field of Search ........................ 210/299, 335, 210/416.1, 488, 489, 492, 495, 500.29; 55/482, 483, 492, 510, 511, 385.4, 486, 487; 96/190; 604/319, 320; 156/313

[56] References Cited

U.S. PATENT DOCUMENTS

| | | |
|---|---|---|
| 2,708,982 | 5/1955 | McGuff et al. . |
| 2,980,204 | 4/1961 | Jordan . |
| 3,220,409 | 11/1965 | Liloai et al. . |
| 3,719,197 | 3/1973 | Pannier, Jr. et al. . |
| 3,738,381 | 6/1973 | Holbrook . |
| 3,768,478 | 10/1973 | Fertik et al. . |
| 3,782,083 | 1/1974 | Rosenberg . |
| 3,809,080 | 5/1974 | Deaton . |
| 3,827,452 | 8/1974 | Baumgarten . |
| 3,889,682 | 6/1975 | Denis et al. . |
| 3,982,538 | 9/1976 | Sharpe . |
| 4,029,487 | 6/1977 | Brandt . |
| 4,033,345 | 7/1977 | Sorenson et al. . |
| 4,115,277 | 9/1978 | Swank . |
| 4,132,649 | 1/1979 | Croopnick et al. . |
| 4,187,390 | 2/1980 | Gore . |
| 4,228,798 | 10/1980 | Deaton . |
| 4,245,637 | 1/1981 | Nichols . |
| 4,275,732 | 6/1981 | Gereg . |
| 4,457,758 | 7/1984 | Norton . |
| 4,459,139 | 7/1984 | VonReis et al. . |
| 4,465,485 | 8/1984 | Kashmer et al. . |
| 4,487,606 | 12/1984 | Leviton et al. . |
| 4,512,771 | 4/1985 | Norton . |
| 4,793,922 | 12/1988 | Morton . |
| 4,813,931 | 3/1989 | Hauze . |
| 5,139,841 | 8/1992 | Makoui et al. . |
| 5,470,324 | 11/1995 | Cook et al. . |
| 5,695,489 | 12/1997 | Japuntich . |
| 5,788,661 | 8/1998 | Japuntich . |

OTHER PUBLICATIONS

Flex Advantage TM Suction Liners and Canisters brochure (2 sheets), Allegiance Healthcare Corporation; the filter referenced in this brochure predates the present invention and is prior art.

Drawing of conventional lid and ITHAT® Filters.

Primary Examiner—David A. Simmons
Assistant Examiner—Fred Prince
Attorney, Agent, or Firm—Paul E. Schaafsma; Donald O. Nickey

[57] ABSTRACT

A filter assembly is disclosed which has a first filter element held by or bonded to a spacer and a second filter element positioned adjacent the spacer on a side of the spacer opposite the first filter.

14 Claims, 2 Drawing Sheets

FILTER ASSEMBLY COMPRISING TWO FILTER ELEMENTS SEPARATED BY A HYDROPHOBIC FOAM

BACKGROUND OF THE INVENTION

1. Field of the Invention

The present invention relates to filters for medical equipment, such as medical suction canisters, and assemblies having filters for use with medical equipment.

2. Related Art

During operative surgery and other medical and biological procedures, suction canister systems are used to collect fluids, including blood, saline and other fluids. These fluids may accumulate during a procedure and must be removed, contained and disposed of after the procedure. A canister system may include a cylindrical canister closed by a cover or lid, and it may have an internal liner attached to the lid. Vacuum is applied to a vacuum port in the lid to develop a sub-atmospheric pressure or vacuum within the canister, which vacuum then also develops at the end of a collection tube connected to a patient port on the lid for suction. One such canister system is shown in U.S. Pat. No. 5,470,324, incorporated herein by reference.

The lid typically includes several access ports with associated attachment or connection elements. For example, the lid may have a large access port that typically remains capped until a fluid-setting agent is added. An outlet or "ortho" port on some canister systems has a wide riser portion for suction in orthopedic operations or for connection of a tandem tube from an additional collection canister. The vacuum port which pulls air from the canister has a float valve to prevent suction of fluid into the vacuum system when the fluid level in the canister gets close to the lid.

The vacuum for the suction canister system typically comes from a hospital or clinic vacuum pump through wall vacuum outlets in surgery suites or elsewhere. Because the vacuum system is common to a number of different areas throughout the facility, it is very important to insure that foreign objects, particles and fluids are not inadvertently taken up by the vacuum system. It is especially significant in fluid collection systems where fluids, or materials entrained in the fluids, may vaporize or become airborne under the influence of the vacuum system.

To stop or minimize possible contamination, a combination of filter elements have been used in the vacuum ports of suction canister systems. The combination of filter elements, commonly known as an aerosol trap, one type of which is included in Allegiance Corporation's canister systems under the trademark ITHAT®, effectively stopped almost all fluid particles or airborne particles, preventing them from entering the vacuum system. (ITHAT is also an acronym for Integrated Two-stage Hygroscopic Aerosol Trap.) Consequently, the vacuum lines and the vacuum system as a whole were protected from contamination arising from airbornes getting into the vacuum system.

The aerosol trap is a combination of two discs of filter material positioned on each side of a polyethylene web or grid and held in place in the vacuum port by an apertured plug. The ITHAT® filter allows high flow rates while effectively trapping about 99.7 percent of the aerosolized microorganisms and particulates.

The aerosol trap can be assembled on the canister side of the vacuum port in a number of ways, but they all involve handling the two discs of filter material and the polyethylene grid individually. They are handled individually both when they are retrieved or collected for assembly and also when the discs of filter material and the grid are positioned in the underside of the vacuum port. The assembly process means that special attention is given to the process and also to later inspection to insure proper assembly. The assembly process is time-consuming and labor-intensive.

SUMMARY OF THE INVENTIONS

A filter assembly, and a suction canister and filter assembly, are described which improve the assembly procedures for suction canisters having those filter assemblies. The new design and the new procedures may decrease the time and effort required for assembly of such canisters. The filter assembly may also permit automated assembly of the lids for the suction canisters, as well.

In accordance with one aspect of the present inventions, an assembly includes a first barrier, such as a filter or other impediment to passage of aerosol, particles and/or vapor laden air. A filter mounting element is used to mount, bond to or otherwise hold the first barrier to the spacer. Having the filter held by the mounting element makes it easier to handle the assembly, and easier to put the filter assembly in place in the desired position in a receptacle, such as a lid, wall, passageway or other structure. The filter mounting element may be a spacer or other structure suitable for holding the filter.

In the preferred embodiment, a second barrier, such as a filter or other impediment to particulates, is positioned on a side of the spacer opposite the first barrier, and is preferably mounted, bonded to or otherwise held to the spacer. This assembly has the effectiveness in trapping aerosolized microorganisms and particulates equivalent to the conventional ITHAT® canister system filter, but is easier to manufacture, especially with automated procedures, and easier to incorporate in a suction canister. This assembly may also make it easier to automate final assembly of the canister lid.

In one preferred embodiment of the inventions, the first barrier is a filter element bonded or otherwise adhered to the spacer, and the second barrier is also a filter element bonded to the opposite side of the spacer from the first filter. This assembly can be more easily incorporated into a lid for a suction canister system and is less susceptible to assembly errors. When used in a suction canister system, the system would include a canister body having an inside and an outside, and a lid for sealing the canister body. The lid includes a wall for defining a passageway between the canister inside and the canister outside. The filter assembly is positioned in the passageway and retained in place by a retainer, plug or other holder. Typically, the filter assembly is placed in-line with the suction port and interior to the enclosure defined by the lid and the canister.

In other embodiments of the inventions, the spacer or other insert extending between the two barriers is preferably an annular hydrophobic foam spacer or other mounting element having a substantial hollow opening or a void to allow passage of air through the opening. Preferably, the amount of area taken up by the spacer is minimized relative to the amount of area available for air flow. While it is possible that the spacer may include projections extending into the air flow area, thereby providing additional separation between the two filter elements, the amount of unobstructed air flow area is preferably maximized.

These and other aspects of the present inventions will be more clearly understood upon consideration of the drawings, a brief description of which follows, and the detailed description of the preferred embodiments.

DETAILED DESCRIPTION OF THE PREFERRED EMBODIMENTS

The following is a detailed description of the best presently known modes of carrying out the inventions. This description is not to be taken in a limiting sense, but is made merely for the purpose of illustrating the general principles of the inventions. Simply by way of example, one or more aspects of the present inventions improve the assembly procedures for suction canisters having filter assemblies. One or more aspects of the inventions may also decrease the time and effort required for assembly of such canisters, and assembly may be automated. These and other aspects are discussed in more detail below.

One application of the present inventions is to a fluid collection system such as one using a suction canister coupled to a vacuum source. While other applications are possible, the inventions will be described herein in the context of a suction canister system with a vacuum or other suction apparatus coupled to a vacuum port associated with the canister. However, it should be understood that these inventions can be applied to applications other than suction canisters.

Figure 1:
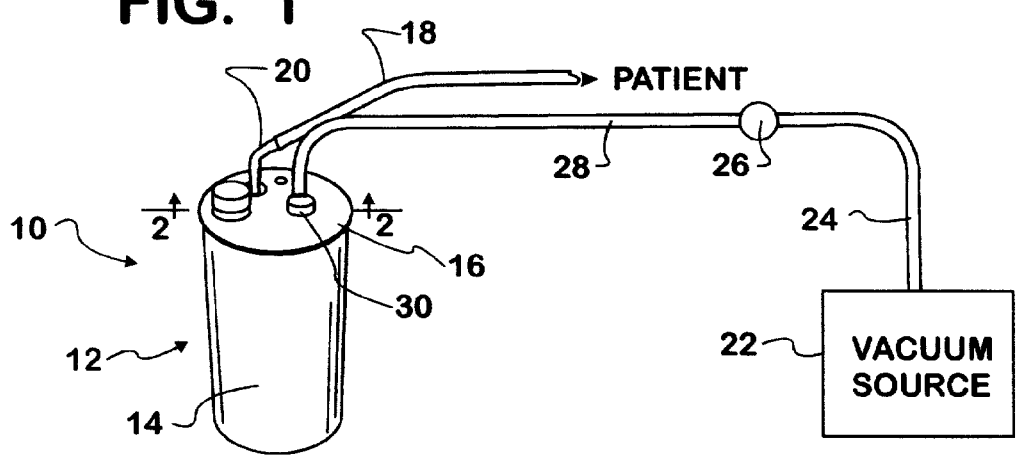
FIG. 1 is a schematic and partial perspective view of a suction canister system in which the assembly of the present invention can be used.

In the context of one preferred embodiment of the inventions used in a suction canister system, see FIG. 1, a vacuum canister fluid collection system 10 can be used for collecting fluids from patients or other sources during operations, medical procedures or for other uses. The system includes a canister assembly 12 having a cylindrical canister 14 and a lid 16 for closing and sealing the canister 14. The canister assembly 12 may be any conventional canister and lid combination presently used for collecting fluids such as in hospitals, clinics and other medical facilities. Examples include Allegiance Corporation's Guardian, CRD, and Flex products available under the MEDIVAC® brand of canisters. One or more of these products can be used for fluid collection, retention and disposal.

The suction canister system includes a patient or collection tube 18 coupled to a patient port 20 in the lid of the assembly. The collection tube 18 collects fluids and particulates from a surgical site, such as a wound or incision, by means of a vacuum developed in the canister assembly. The fluids and particulates are passed along the collection tube 18 and deposited in the canister, or a liner in the canister (not shown), for later disposal. Additional canisters can be assembled in series or in parallel, as is known to those skilled in the art.

Part of the overall system includes a vacuum source for creating a sub-atmospheric pressure or vacuum within the canister assembly 12. A vacuum can be produced in a number of ways, but the present discussion will refer to such vacuum sources as are available in hospitals, clinics and other medical facilities. Vacuum can be produced in a vacuum source 22, which may be a vacuum pump located in a utility area of a hospital. Vacuum is made available throughout the hospital through tubing 24 or other conduit designed to meet the requirements of a medical facility. Various controls, valves or other equipment 26 are included to control and maintained the vacuum system. For example, the equipment typically includes wall vacuum outlets and the like. The suction canister assembly 12 is coupled to the vacuum source through appropriate tubing 28 in the conventional way. The tubing 28 is coupled to a vacuum port 30 in the lid of the canister assembly for providing a sub-atmospheric pressure within the canister assembly, thereby creating suction at the end of the patient collection tube 18.

Figure 2:
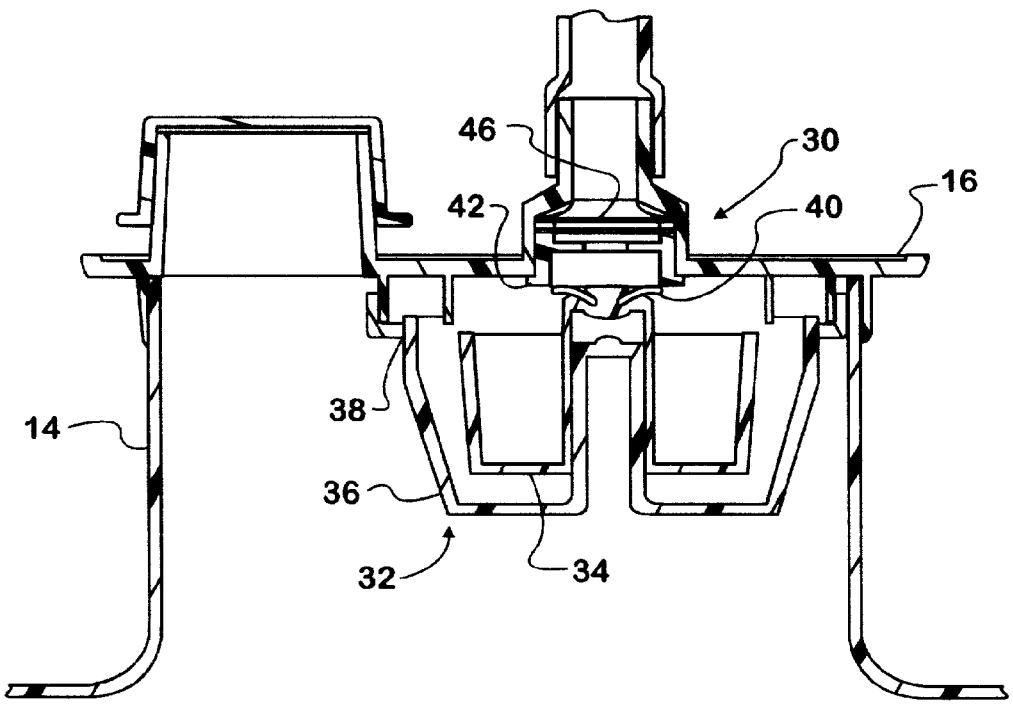
FIG. 2 is a partial cross-sectional view of the suction canister of FIG. 1 showing a vacuum port in the lid of the suction canister having a filter assembly in accordance with one aspect of the present inventions.

Because the vacuum source is typically a fixture in the medical facility and because the equipment 26 and tubing 24 are also fixtures, efforts are made to protect the vacuum system from contamination or deterioration due to fluids, particulates or vaporized fluids getting into the vacuum system. For example, each canister has a conventional automatic overflow shut off valve 32 (FIG. 2) mounted to the underside of the lid 16 which includes a float valve 34 within a cage 36 having a clamp 38 engaging the underside of the lid 16. The float valve includes a flexible seal 40 for engaging and sealing with an apertured plug or retainer 42 extending into the base of the vacuum port 30 whenever the level of fluid in the canister reaches a selected maximum level. The float valve prohibits fluid from a full canister from entering the vacuum system.

A further protection for the vacuum system is the aerosol trap or filter 46 positioned preferably in the base 44 of the vacuum port 30. The filter is held in place by the retainer 42, which has an aperture 48 permitting air flow from the interior of the canister through the passage way defined by the vacuum port into the vacuum system. The retainer is typically a circular plastic element welded or otherwise held in the bottom of the vacuum port in the conventional manner. It holds the aerosol trap 46 in place against a shoulder 50 in a necked-down portion 52 of the vacuum port.

Figure 4:
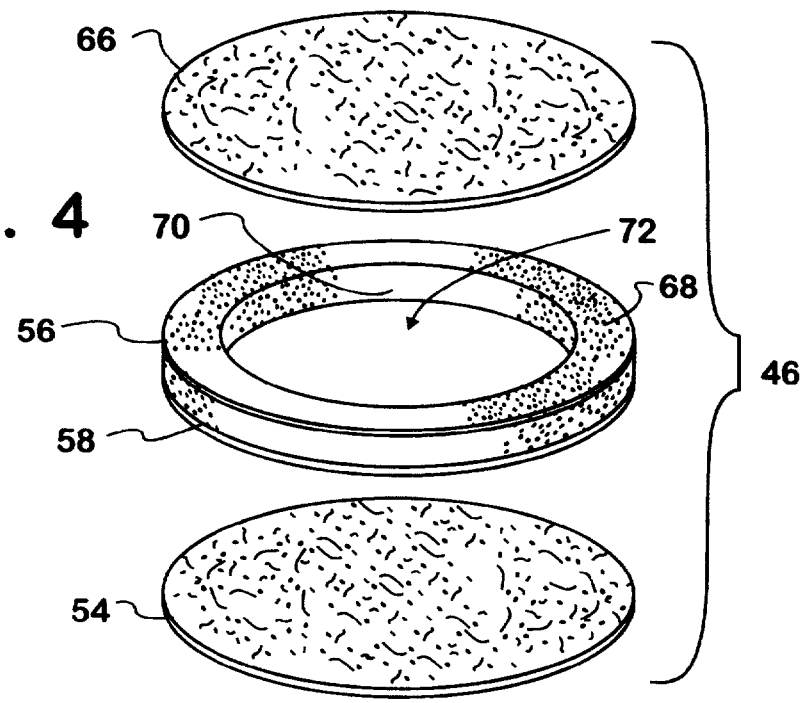
FIG. 4 is an exploded and partial perspective view of the filter assembly in accordance with one aspect of the present inventions.

The aerosol trap 46 (FIG. 4) preferably includes a first filter, aerosol barrier or impediment, preferably in the form of a filter element 54, for impeding or stopping particulates, moisture droplets, and the like. The first filter element 54 is preferably a planar and circular filter element having the same configuration and characteristics as the conventional filter wafer used in current MEDIVAC® suction canisters. The filter material is preferably chosen so as to allow air to pass through the filter, while at the same time stopping particulates and liquid droplets. However, it should be understood that the first aerosol barrier can be formed from other materials, can have other configurations and shapes, and need not be essentially flat, and still achieve some or all of the benefits provided by the MEDIVAC® ITHAT® filter. The first filter is preferably a paper material, but it may be a porous or fibrous material, and may be formed from other materials besides paper. Optimally, the first filter element is one which, when combined with the other elements of the aerosol trap, traps 99.7 percent of aerosolized microorganisms and particulates with the same efficiency as the MEDIVAC® ITHAT® filter.

The first filter element is preferably bonded, adhered to or otherwise held in place on a spacer 56 in order to help position or hold the first filter element in place. The spacer may be a ring, annulus, a planar sheet coextensive with one or more filter elements, spot spacers either evenly or randomly distributed, a plurality of arcuate segments or one or more other segments for holding the first filter element. The spacer 56 preferably holds the filter element 54 in a location relative to the retainer 42 so that gaseous fluid such as air from the canister impacts the filter element 54. The spacer 56 preferably holds and positions the first filter element 54 so that the first filter element can function properly under typical operating conditions.

A surface of the spacer 56 is preferably coated with a uniform layer of adhesive 58 to hold the first filter element 54 against the spacer. The adhesive 58 bonds an edge portion 60 of the first filter element 54 to the spacer 56 to firmly and reliably hold the first filter element 54. The surface area of bonding is preferably sufficient to properly hold the first filter element 54 in place while preventing the first filter element from sagging or bowing appreciably as air passes through it. However, the bonding surface area is preferably not so great as to significantly reduce the air flow through the filter element or affect the efficiency of the aerosol trap. In the preferred embodiment, the edge portion 60 has a surface area of bonding that corresponds to the width 62 of the spacer 56. Also in the preferred embodiment, the width of the spacer is significantly less than 50% and preferably less than 10 percent of the overall outside diameter 64 of the spacer. For example, where the outside diameter of the spacer is 0.781 in., the width 62 of the spacer may be about 0.040 in. or more.

The material of the spacer is preferably chosen to also be compatible with the filter elements and with the environment in which the suction canister will be used. In the preferred embodiment, the spacer 56 is formed from a hydrophobic material such as polyethylene foam. The spacer preferably prevents or reduces the likelihood that moisture or liquid will wick or migrate from one filter element to the other, under influence of the pressure differential across the vacuum port, gravity or other forces. The spacer then also acts as a barrier or impediment to moisture flow across the trap 46, in addition to keeping the two filter elements apart, while at the same time preferably allowing as much free air to pass through the trap. The foam has a uniform density throughout, and may even have a density higher than a typical foam, if desired.

The density of the foam can be low but it is preferred that the foam be strong enough to keep the filter elements apart. It is also preferred that the material, the shape or configuration and the surface characteristics of the foam be such that little or no wicking occurs between the filter elements. With a lighter density foam, the spacer could be porous enough to permit sufficient air flow through the assembly even if the spacer extended across the entire surface area of the filter assembly. For example, if the spacer extended entirely across the filter element, the full surface area of the spacer would equal the surface area of the filter element. Preferably, about 25% or less of that surface area on a given side of the foam would be contacting the filter material, and the remaining 75%, for example, of the area within the outer boundary of the spacer would permit air flow. With a light density foam the adhesive preferably contacts the surface of the foam and does not appreciably extend across cells of the foam. Therefore, any occlusion by the adhesive is minimized.

The adhesive is also preferably biologically and chemically compatible with the material and the environment in which suction canisters are used. One preferred foam and adhesive combination is SURESTIK® double-coated polyethylene foam by Surestik, a Viscor company, under model description 4E01-2/4E04-2 PS/2, at about 1/16th inch thick. The adhesive may be applied in non-uniform locations around the spacer or in a uniform distribution. In any case, the bonding is preferably sufficient to produce the desired efficiency of trapping particulates and aerosolized fluids. The first filter element can be held on the spacer by means other than adhesive. For example, the filter element can be attached, fixed, welded or otherwise mounted to the spacer. The form and the extent to which the filter element is held on the spacer is preferably sufficient at least to hold the filter element 54 on the spacer 56 until such time as the aerosol trap is in place in the vacuum port 30 and held in place by the retainer 42. Thereafter, it is not believed that the function of the adhesive is as important to the function of the aerosol trap.

Exemplary specifications for the SURESTIK brand of polyethylene foam include a tensile strength of 119 psi, a tear of 22 pounds per inch, an elongation of 302%, a density of 4 pounds per cubic foot, a caliper of 0.0665 inch and an operating temperature range of −20 to 225° F. These are values that correspond to the preferred material but other materials may also be used that have either similar specifications, or that have entirely different specifications while still achieving one or more of the desired results. For example, the elongation can be as low as ten percent or in the tens percent or as high as some rubber compounds. The density can be as low as half or a quarter or less of the SURESTIK® brand of polyethylene foam or as much as the conventional ITHAT® canister system disk or more. Likewise, the tear can be more or less than the 22 pounds/inch for the preferred foam. However, a preferred material will be within approximately plus 100% or minus 50% of at least one of the specifications for the preferred SURESTIK® brand of polyethylene foam.

A second filter element 66 is positioned adjacent to spacer 56 on a side of the spacer opposite the first filter element 54. As with the first filter element 54, the second filter element 66 preferably serves as a barrier or impediment to passage of particulates or liquid droplets into the vacuum system. The second filter element 66 preferably has the same construction and configuration as the first filter element 54.

In the preferred embodiment, the second filter element 66 is held or otherwise adhered to the spacer through a layer of adhesive 68 preferably identical to the adhesive 58 holding the first filter element 54. The adhesive layer 68 is preferably sufficient to hold the second filter element 66 in place at least until such time as the retainer 42 is properly installed to hold the aerosol trap 46 in the vacuum port.

In the preferred embodiment, the aerosol trap is preferably formed so that the outside edge of the spacer 56 and the respective perimeters of the filter elements 54 and 66 are flush with each other. In this configuration, the aerosol trap 46 can be adequately held in place in the vacuum port. This configuration also helps to ensure that most or all of the air flow through the trap 46 occurs within the wall 70 defining the void 72 in the interior of the spacer 56. For example, the surface area of the void is preferably more than 50 percent of the entire surface area of the filter assembly to permit a large air flow rate through the aerosol trap 46.

The thickness of the spacer 56 is preferably sufficient to produce the overall effectiveness for the aerosol trap achieved in the current three-piece assembly. The first and second filter elements 54 and 66 are held apart a distance sufficient to minimize the migration or movement of liquid droplets from the first filter element 54, proximal to the interior of the canister, to the second filter element 66, distal to the interior of the canister.

Making the aerosol trap 46 in this way makes assembly of the canister system easier than with conventional aerosol traps. With the aerosol trap 46, assembly of the suction canister lid with the aerosol trap may be automated, thereby reducing production time and improving efficiency.

Figure 3:
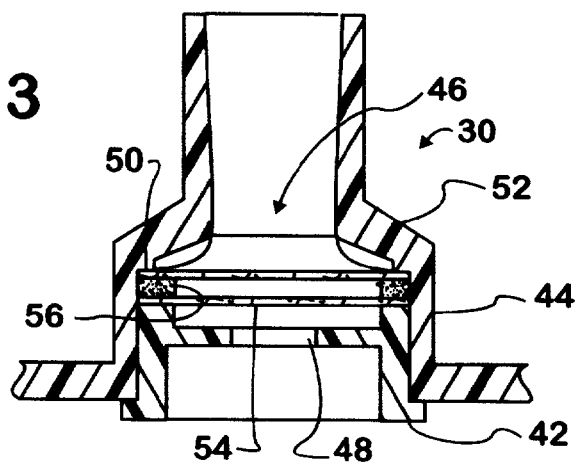
FIG. 3 is a detailed cross-sectional view of the vacuum port of FIG. 2 showing the combination of the filter assembly and the vacuum port.
Figure 5:
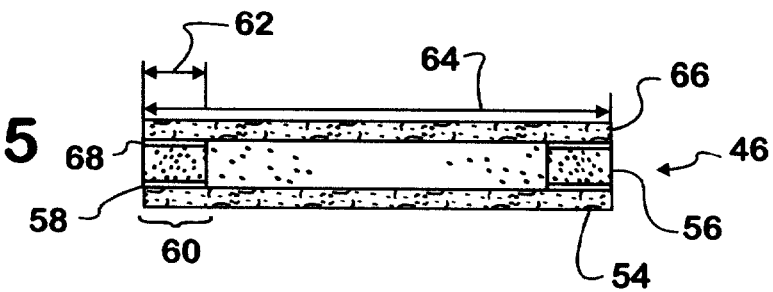
FIG. 5 is a detailed cross-sectional view of a filter assembly in accordance with one aspect of the present inventions.

The aerosol trap 46 may be produced by providing a roll of polyethylene foam having the appropriate thickness, and pre-coated on both sides with the desired adhesive. The foam roll will typically include release paper or backing paper on both sides. The release paper is then removed from the top and a rotary die punches a hole through the center corresponding to the void 72. The bottom liner then is removed from the sheet, taking with it the center elements to produce the void 72. The remaining layer includes the foam sheet but without the centers, and opposite layers of adhesive on the foam sheet. Two sheets of filter paper are then fed in from top and bottom, respectively, to the foam sheet to form a laminate. A second die then punches out the sheet and makes filter wafers having the configuration shown in FIGS. 3–5. Air jets then remove the filters from the sheet in the location of a tight curve or bend in the path of the laminate sheet. The scrap continues, to be discarded, while the filter assemblies are packaged for shipping or readied for assembly into suction canister lids.

Although the present inventions have been described in terms of the preferred embodiments above, numerous modifications and/or additions to the above-described preferred embodiments would be readily apparent to one skilled in the art. It is intended that the scope of the present inventions extend to all such modifications and/or additions.

What is claimed is:

1. A canister lid and filter assembly comprising:
   a) a lid for covering an opening in a canister and having a wall defining a vacuum port;
   b) an aerosol trap disposed within said vacuum port; said aerosol trap comprising a first filter element, a second filter element and a spacer wherein said spacer is an annular, hydrophobic foam characterized in that it reduces wicking between the filter elements and wherein at least one of said filter elements is bonded to said spacer; and
   c) said aerosol trap being retained within said vacuum port by a retainer.

2. The filter assembly of claim 1 wherein said second filter element is bonded to said spacer.

3. The filter assembly of claim 1 wherein said first and second filter elements are formed from the same material.

4. The filter assembly of claim 1 wherein said first and second filter elements are formed from paper.

5. The filter assembly of claim 1 wherein the spacer has an outside edge and the first and second filters have outside edges that are flush with the spacer outside edges.

6. The filter assembly of claim 5 wherein the spacer has a cross sectional width and a diameter wherein the diameter is much greater than the cross sectional width.

7. The filter assembly of claim 6 wherein the spacer width is less than 10% of the diameter of the spacer.

8. The filter assembly of claim 1 wherein the filters are spaced apart by the spacer a distance sufficient so that they do not touch during normal operation.

9. The filter assembly of claim 1 wherein said spacer and said filter elements are configured to create a void and said void has a surface area and wherein the void surface area is more than 50% of the surface area of the filter assembly.

10. The filter assembly of claim 9 wherein said wall defining the vacuum port is circular.

11. The filter assembly of claim 10 wherein the first filter element is adhered to the spacer.

12. The filter assembly of claim 10 wherein the first and second filter elements are adhered to the spacer forming a closed void between the filter elements.

13. The filter assembly of claim 1 wherein the spacer is polyethylene foam.

14. A vacuum canister and filter assembly comprising:
   a) a container body having an inside and an outside and a lid for sealing the container body, the lid including a wall for defining a passageway between the container inside and the container outside; and
   b) a filter assembly in the passageway comprising a first filter element, a second filter element and a spacer wherein said spacer is an annular, hydrophobic foam characterized in that it reduces wicking between the filter elements and wherein at least one of said filter elements is bonded to said spacer; said filter assembly being retained within said passageway by a retainer.

* * * * *